(12) United States Patent
Maus et al.

(10) Patent No.: US 11,035,761 B2
(45) Date of Patent: Jun. 15, 2021

(54) MEASURING APPARATUS AND METHOD FOR DETERMINING THE DEGREE OF BACTERIAL CONTAMINATION OF PROCESS LIQUIDS

(71) Applicant: AdvaTech Projects GmbH & Co.KG, Heinsberg (DE)

(72) Inventors: Michael Maus, Horb a.N (DE); Thomas Wimmer, Heinsberg (DE); Ulrich Berner, Koengen (DE); Frank Josupeit, Holzgerlingen (DE)

(73) Assignee: ADVATEC PROJECTS GMBH & CO. KG, Heinsberg (DE)

( * ) Notice: Subject to any disclaimer, the term of this patent is extended or adjusted under 35 U.S.C. 154(b) by 90 days.

(21) Appl. No.: 16/248,038

(22) Filed: Jan. 15, 2019

(65) Prior Publication Data

US 2019/0242793 A1 Aug. 8, 2019

(30) Foreign Application Priority Data

Feb. 6, 2018 (DE) ...................... 10 2018 102 658.7

(51) Int. Cl.
*C12M 1/34* (2006.01)
*G01N 1/24* (2006.01)
(Continued)

(52) U.S. Cl.
CPC ................ *G01N 1/24* (2013.01); *C12Q 1/04* (2013.01); *C12Q 1/06* (2013.01); *C12Q 3/00* (2013.01);
(Continued)

(58) Field of Classification Search
CPC ........... C12M 41/34; C12M 29/24; B01L 5/02
See application file for complete search history.

(56) References Cited

U.S. PATENT DOCUMENTS 3,740,320 A 6/1973 Arthur
3,942,792 A * 3/1976 Topol ...................... G01N 7/00
73/19.1

(Continued)

FOREIGN PATENT DOCUMENTS

DE 199 21 999 A1 11/2000
EP 2 833 117 A1 2/2015

OTHER PUBLICATIONS

Extended European Search Report dated Jul. 8, 2019 in European Application No. 18212478.4 with English translation of the relevant parts.

*Primary Examiner* — Jonathan M Hurst
(74) *Attorney, Agent, or Firm* — Collard & Roe, P.C.

(57) ABSTRACT

A measuring apparatus and a method for determining the degree of bacterial contamination of process liquids uses at least one gas sensor for measuring the gas concentration of a gas producible by aerobic bacteria in the process liquid. An evaluating device is connected with the sensor for evaluating a sensor signal generated by the sensor and correlated with the degree of bacterial contamination. To determine the degree of bacterial contamination a funnel-shaped gas collecting bell is partly immersed in the process liquid so that a gas collection cavity for collection of the escaping gas is formed directly above the process liquid surface in the gas collecting bell. The gas escaping can be fed by a gas pump via a gas feed line to the sensor, conducted via the sensor and pumped back again to the gas collection cavity by way of a gas return line.

14 Claims, 1 Drawing Sheet

(51) Int. Cl.
*C12Q 1/04* (2006.01)
*C12Q 3/00* (2006.01)
*C12Q 1/06* (2006.01)
*G01N 1/28* (2006.01)
*C12M 1/00* (2006.01)
*B01L 5/02* (2006.01)
*G01N 33/00* (2006.01)

(52) U.S. Cl.
CPC ............... *G01N 1/286* (2013.01); *B01L 5/02* (2013.01); *C12M 29/24* (2013.01); *C12M 41/34* (2013.01); *G01N 33/004* (2013.01)

(56) References Cited

U.S. PATENT DOCUMENTS

| | | |
|---|---|---|
| 4,220,715 A | 9/1980 | Ahnell |
| 4,330,385 A | 5/1982 | Arthur et al. |
| 4,546,640 A | 10/1985 | Stone et al. |
| 4,650,767 A | 3/1987 | Arthur |
| 5,421,194 A | 6/1995 | Doyle et al. |
| 6,420,187 B1 | 7/2002 | Gilmore et al. |
| 6,677,132 B1 | 1/2004 | Hofler et al. |
| 2015/0099274 A1 | 4/2015 | Axelrod et al. |

\* cited by examiner

MEASURING APPARATUS AND METHOD FOR DETERMINING THE DEGREE OF BACTERIAL CONTAMINATION OF PROCESS LIQUIDS

CROSS REFERENCE TO RELATED APPLICATIONS

Applicant claims priority under 35 U.S.C. § 119 of German Application No. 10 2018 102 658.7 filed Feb. 6, 2018, the disclosure of which is incorporated by reference.

BACKGROUND OF THE INVENTION

1. Field of the Invention

The invention relates to measuring apparatus and a method for determining the degree of bacterial contamination of process liquids.

2. Description of the Related Art

Increasingly higher numbers of bacteria appear in the process baths of current industrial installations. In order to determine the bacterial count culture media are incubated with process liquid and subsequently incubated in an incubator. After approximately two days the cell count is determined by counting the cell colonies that have grown. This procedure is necessary in order to ensure process stability. In the case of increased bacteria count values of >$10^4$ CFU/ml (CFU='colony-forming units') substantial disruptions to process can occur, which usually have to be precluded by addition of biocides. Alternatively, samples are removed from baths and dispatched to an accredited laboratory or institute which communicates the findings to the plant operator at the earliest after three days.

In the exponential growth phase (duplication rates ~100 min) of the bacteria the above-mentioned methods are too slow. Biocides cannot always be admetered in good time, so that losses of quality occur in production. If the chemistry of the process baths can no longer be regenerated these have to be discarded at least in part. This is very expensive and additionally loads the environment.

Most methods for determining bacterial count function by way of a bypass, where a liquid is fed either to a container or directly to a form of sensor system such as described in, for example, DE 199 21 999 A1. This conceals very significant disadvantages and risks in robust use in industrial process baths. On the one hand, in the case of aggressive media the attachments (lines, pumps, valves, etc.) can be easily damaged so that the service life thereof is very short. On the other hand, due to deposits and bacterial contaminations of the measuring facility the results can be substantially falsified. Washing devices can help here, but are very cost-intensive not only in procurement, but also in maintenance. In the case of CDC coatings (CDC=cathodic dip coating) such attachments are almost impossible, since this process liquid has a tendency to coagulation and sedimentation.

In absolutely clear process baths the bacterial count can be determined on-line by cell counters. This method has the disadvantage that dead cells and contaminating particles are also included in the count.

Another rapid method for determination of the degree of bacterial contamination is determination of the ATP content (ATP=adenosine triphosphate). Here, too, dead cells are detected at the same time. Moreover, sample removal with subsequent spectroscopic evaluation of the ATP content in a laboratory is necessary, so that this cannot be regarded as an 'on-line method'.

SUMMARY OF THE INVENTION

It is an object of the invention to make available measuring apparatus and a method of the kind stated in the introduction by which on-line detection of the degree of bacterial contamination ('on-line bacteria monitoring') of any desired process liquids is made possible and after a comparatively short time (a few hours) a reliable signal value in correlationship with the bacterial count is available. In addition, the measuring apparatus and the application of the method shall be robust for almost all liquid media such as occur in ventilated industrial baths.

This object is fulfilled with respect to a measuring apparatus particularly by the features of one aspect of the invention and with respect to the method particularly by the features of another aspect of the invention.

Accordingly, the invention relates to measuring apparatus for determining the degree of bacterial contamination of process liquids, comprising at least one gas sensor for measuring the gas concentration of a gas producible or produced by aerobic bacteria possibly or actually present in the process liquid and an evaluating device connected therewith for evaluation of a sensor signal, preferably electrical sensor signal, which is generated by the gas sensor and correlated with the degree of bacterial contamination, wherein a geometric gas collecting hollow body, preferably of rotationally symmetrical form, is provided, which has an immersion cavity and which is partly immersible or immersed in the process liquid in such a way that a gas collection cavity, which is also termed projection, for collecting the gas escaping or escaped from the process liquid into the environment is formed in the gas collecting hollow body directly above a liquid surface, which is present in the immersion cavity, of the process liquid, and that a gas feed line, one feed line end of which communicates with the gas collection cavity of the gas collecting hollow body and the other feed line end of which communicates with a device cavity of a sensor device, which includes the at least one gas sensor, particularly a sensor array, for measuring the concentration of the gas escaping from the process liquid, is provided, which sensor device is in gas connection with the at least one gas sensor, and that a gas return line, one return line end of which communicates with the device cavity of the sensor device and the other return line end of which communicates with the gas collection cavity of the gas collecting hollow body, is provided, and that a gas pump for pumping the gas from the gas collection cavity of the gas collecting hollow body via the at least one gas sensor back to the gas collection cavity of the gas collecting hollow body is provided.

According to a particularly preferred embodiment of the measuring apparatus it can be provided that the gas collecting hollow body is cylindrical, bell-shaped or funnel-shaped or formed as a cylinder, bell or funnel. In particular, if the geometric hollow body is formed as a bell, which is preferably funnel-shaped, or as a funnel it is possible for a significant boost of the sensor signal and the detection limits to be achieved.

According to a particularly preferred variant of embodiment it can be provided that a first agitator for homogenization of the process liquid and/or a second agitator for expulsion of the gas produced by the aerobic bacteria and released into the process liquid and/or for expulsion of the gas produced by the aerobic bacteria and adsorbed at solid particles contained in the process liquid is or are provided. For preference, the first agitator and the second agitator can be integrated in a common agitator or a single agitator can be provided for the aforesaid functions. Particularly short measuring times or rapid measurements of the degree of bacterial contamination are possible by these measures.

According to a development of the measuring apparatus it can be provided that a controllable raising and lowering device for raising and lowering the gas collecting hollow body and optionally the agitator is provided, by means of which the gas collecting hollow body and optionally the agitator are movable from a raised setting outside the process liquid into a lowered setting in which the gas collecting hollow body is partly and optionally the agitator at least partly or entirely immersed in the process liquid and in which the gas concentration of a gas produced by the bacteria is measurable or measured by way of the at least one gas sensor and by means of which the gas collecting hollow body and optionally the agitator are movable from the lowered setting to the raised setting. In that case, it can be provided that the raising and lowering device comprises a distance sensor for measuring the spacing of the gas collecting hollow body, particularly at the lower edge thereof, from the liquid surface of the process liquid. For preference the distance sensor can be an ultrasonic sensor. It is possible for even better, automated measurements to be carried out by these measures.

According to an advantageous development of the measuring apparatus it can be provided that the evaluating device is provided with an interface for connection with a control, by means of which a biocide can be admetered to the process liquid in dependence on the gas concentration, which is measured by way of the at least one gas sensor, of the gas produced over time by the bacteria or that the evaluating device is connected directly or via the interface with a control by means of which a biocide can be admetered to the process liquid in dependence on the gas concentration, which is measured by way of the at least one gas sensor, of the gas produced over time by the bacteria. The control enables industrial realization of fully automatic biocide admetering in dependence on the measured bacterial concentration in the process liquid. If the measuring apparatus has the interface for connection with the control, the measuring apparatus can be used optionally without or with the control connected by way of the interface.

The measuring apparatus according to the invention can detect all aerobic bacteria and issue on-line a signal correlated with the bacterial count.

The invention also relates to a method of determining the degree of bacterial contamination of process liquids, wherein the gas concentration of a gas producible or produced by bacteria possibly or actually present in the process liquid is measured by way of at least one gas sensor which produces a—preferably electrical—sensor signal correlated with the degree of bacterial contamination, wherein the sensor signal is evaluated by means of an evaluating device connected with the at least one gas sensor, wherein a geometric gas collecting hollow body, preferably of rotationally symmetrical form, having an immersion cavity is partly immersed in the process liquid in such a way that a gas collection cavity, also termed projection, for collecting the gas issuing from the process liquid into the environment is formed in the gas collecting hollow body directly above a liquid surface, which is present in the immersion cavity, of the process liquid, wherein the gas escaping from the process liquid into the environment is collected in the gas collection cavity and from there fed by means of a gas pump via a gas feed line to the at least one gas sensor, particularly a sensor array, conducted across the at least one gas sensor and pumped back again to the gas collection cavity of the gas collecting hollow body by way of a gas return line.

According to a particularly preferred embodiment of the method it can be provided that the gas collecting hollow body is cylindrical, bell-shaped or funnel-shaped or formed as a bell, funnel or cylinder. If, in particular, the geometric hollow body is formed as a bell, which is preferably funnel-shaped, or as a funnel it is possible for a significant boost of the sensor signal and the detection limit to be achieved.

According to a particularly preferred variant of the embodiment of the method it is provided that the gas produced by the aerobic bacteria and released into the process liquid and/or the gas produced by the aerobic bacteria and adsorbed at solid particles contained in the process liquid is or are expelled, particularly discontinuously, preferably at periodic intervals, by means of an agitator, wherein the gas concentration of the expelled gas is measured by way of the at least one gas sensor. Particularly short measuring times or rapid measurements of the degree of bacterial contamination are possible by these measures.

According to a development of the method it can be provided that the gas collecting hollow body and optionally the agitator are transferrable or transferred by means of a controllable raising and lowering device from a lowered setting, in which the gas collecting hollow body is partly and optionally the agitator at least partly immersed in the process liquid and in which the gas concentration of the gas produced by the bacteria is measured by way of the at least one gas sensor, to a raised setting, in which the gas collecting hollow body and optionally the agitator are disposed outside the process liquid, and conversely. Further, it can be provided that the gas collecting hollow body and optionally the agitator before being disposed in a or their lowered setting are moved by means of a or the controllable raising and lowering device, starting from a or the raised setting in which they are disposed outside the process liquid, to a or the lowered setting in which the gas collecting hollow body is partly and optionally the agitator at least partly immersed in the process liquid. It is possible for even better, automated measurements to be performed by these measures.

According to an advantageous development of the method it can be provided that the evaluating device is connected directly or by way of an interface with a control, by means of which a biocide is admetered to the process liquid in dependence on the gas concentration, which is measured by way of the at least one gas sensor, of the gas produced over time by the bacteria. The control makes possible industrial realization of fully automatic biocide admetering in dependence on the measured bacterial concentration in the process liquid.

According to a particularly preferred variant of the method it can be provided that the degree of bacterial contamination is determined by means of the measuring apparatus according to the invention.

A continuous, thus uninterrupted, process check with respect to determination of the degree of bacterial contamination by bacteria which may be present in the process liquid is possible by the measuring apparatus according to the invention and by the method according to the invention.

In the context of the present invention it is understood by "on-line detection of the degree of bacterial contamination" ("on-line bacteria monitoring") that the measurement value is generated fully automatically, thus without sampling being required.

BRIEF DESCRIPTION OF THE DRAWINGS

Further advantages, features and aspects of the invention are evident from the claims and the following description section, in which a preferred embodiment of the invention is described by way of example with reference to the figures, in which:

DETAILED DESCRIPTION OF THE PREFERRED EMBODIMENTS

Figure 1:
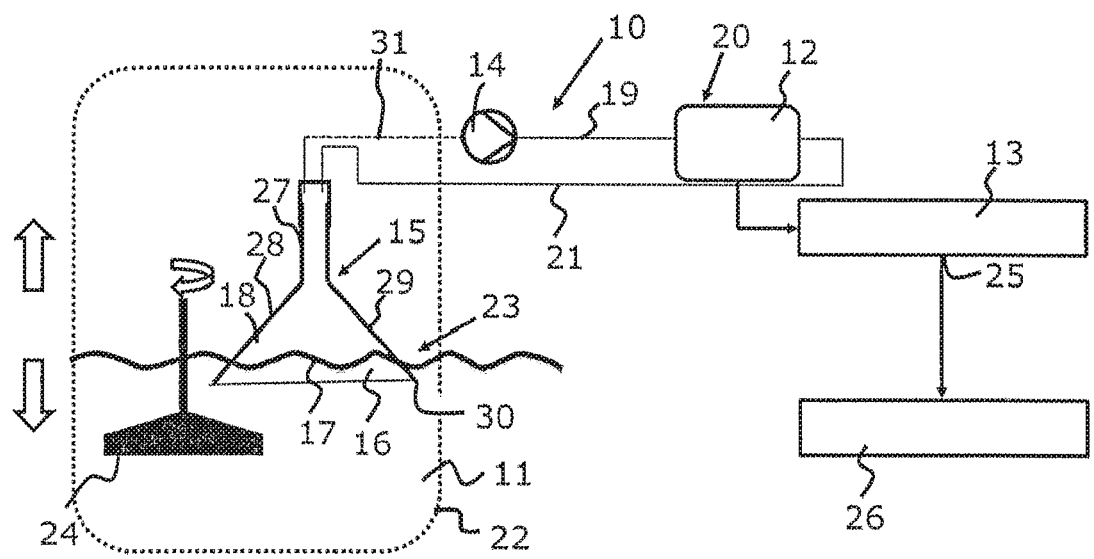
FIG. 1 shows a schematic construction of a plant with measuring apparatus according to the invention.

The measuring apparatus 10 substantially consists of a bell 15, also termed gas collecting hollow body, a sensor device 20 with a gas sensor array 12 with at least one gas sensor, a gas pump 14 and an evaluating unit 13. The evaluating unit 13 can have an interface 25 with respect to a plant control 26. The bell 15 preferably has the form of a funnel, but it can also have the form of a cylinder or other geometric hollow body. As considered in its intended use setting the bell 15 has an upper, preferably cylinder-shaped or cylindrical, neck 27. The neck 27 transitions in downward direction into a downwardly widening and downwardly open funnel 28. The funnel 28 has a conical funnel wall 29. At its lower edge the funnel 28 has an encircling, preferably circular, edge 30.

For measuring operation, the funnel-shaped bell 15 optionally together with the agitator 24 is transferred by means of a controllable raising and lowering device 22, which comprises an ultrasonic sensor, or manually to a lowered setting 27 in which the bell 15 partly enters by the lower edge 30 thereof into the process liquid.

In a given case, simultaneously or later the stirring element of the agitator 24 is immersed by means of a or the controllable raising and lowering device 22 in the process liquid (FIG. 1). In the thus-immersed lowered setting 27 a gas collection cavity 18, which is also termed projection, for collection of the gas escaping from the process liquid 11 into the environment is formed in the bell 15 directly above the liquid surface 17, which is present in the interior of the funnel 28, of the process liquid 11, the interior of the funnel also being termed immersion cavity.

If the process liquid 11 contains aerobic bacteria these produce gases, for example carbon dioxide ($CO_2$). A part of this carbon dioxide migrates upwardly to the liquid surface 17 and escapes therefrom into the gas collection cavity 18 of the bell 15. The gas volume enclosed therein is conducted by a gas pump 14 in the circuit via the gas sensor array 12, which generates an electrical signal. The gas sensor array 12 can be equipped with all conventional sensor types. The gas sensor array 12 has to be equipped with at least one gas sensor, by means of which the concentration of the gas produced by the bacteria is measurable. The signals generated by the at least one gas sensor or by the gas sensor array 12 are passed on at the evaluating unit 13 with intelligent algorithms and optional visualization of the measurement results, such as a PC, microcontroller, data logger, etc., with an optional interface 25 to the optional plant control 26.

The gas volume enclosed in the gas collection cavity 18 of the bell 15 is pumped by means of the gas pump 14 through a gas feed line 19, one feed line end of which opens into the gas collection cavity 18 of the bell 15 and the other feed line end of which opens into a device cavity of the sensor device 20, which includes at least one gas sensor 12. The said device cavity is in gas connection with the at least one gas sensor 12.

In addition, a gas return line 21 is provided, one return line end of which opens into the device cavity of the sensor device and the other return line end of which opens into the gas collection cavity 18 of the bell 15.

The gas pump 14 serves for pumping the gas from the gas collection cavity 18 of the bell 15 via the at least one gas sensor 12 back to the gas collection cavity 18 of the bell 15 in a circuit operation.

If the measuring apparatus is a handheld device, the interface can be designed for a PC or other recording apparatus, such as an SD card, USB, etc.

Optionally, an apparatus is equipped with an agitator 24 for homogenization of the process liquid. This agitator 24 can also be used, with particular advantage, for expelling the gas produced by the aerobic bacteria and released into the process liquid 11 and/or for expelling the gas produced by the aerobic bacteria and adsorbed at solid particles contained in the process liquid 11.

For dehumidification of the gas produced by the bacteria, thus the measurement gas, use is made of a hose 31 which is permeable by water vapour, but impermeable by the measurement gas. The hose 31 preferably consists of a sulfonated polytetrafluoroethylene (PTFE). The hose 31 can be double-walled.

The measuring system 10 can be used directly above an industrial bath or, however, also in a laboratory directly above a beaker, thus directly above any liquid surface. Pumping of the process liquid is not necessary.

The optional control 26 detachably connected by way of the interface 25 enables industrial realization of fully automatic admetering of a biocide depending on the measured bacterial concentration of the process liquid 11 or in a process bath.

Measurement Modes and Measurement Cycles:

Two measuring modes are possible, namely a long-term measurement (lengthy measurement) and a short-term measurement (rapid measurement):

Long-Term Measurement (Lengthy Measurement):

Over 90% of discovered microorganisms in CDC plants are aerobic microorganisms. Principal bacteria in CDC installations are, regardless of the coating kinds, bacteria of the *Burkholderia* species. These microorganisms consume oxygen in their respiration and in that case produce carbon dioxide (exhalation of carbon dioxide). This carbon dioxide is measured in the projection of a container with use of the gas sensor array 12 and the diaphragm pump 14 and is correlated with the activity or bacterial count of the planktonitic microorganisms. A decisive aspect of the construction is the funnel-shaped 'bell' 15, which makes it possible to significantly boost the signal and improve the detection limits by approximately a power of ten.

Short-Term Measurement (Rapid Measurement):

Aerobic microorganisms in their respiration consume oxygen and in that case produce carbon dioxide (exhalation of carbon dioxide). This carbon dioxide is partly released in the fluid phase or adsorbed at solid particles (in the liquid or in the coating). With the same measuring construction and additional agitator 24 this carbon dioxide can be expelled and measured. The advantage of short measuring times below 30 minutes can thereby be realized.

Measurement Cycle of Long-Term Measurement:

Initially, the lower edge 30 of the bell 15 is disposed in a raised setting of, for example, +15 cm above the liquid level or the liquid surface 17 of the bath or container. In this raised setting all sensors (at least one carbon dioxide sensor, moisture sensor and temperature sensor; also extensible, as desired, to other gases) and the gas pump 14 are in operation at least 10 minutes in the ventilated state.

The spacing of the bell 15 from the liquid surface 17 is regulated by means of an ultrasonic sensor. The relative humidity and the carbon-dioxide/air concentration are interrogated. Prior to lowering the bell 15 the relative humidity must be below 45%, otherwise water condenses on the sensor system. The carbon-dioxide/air concentration must lie below a value of 650 ppm so that this does not become signal noise even in the case of small bacterial concentrations, in other words carbon dioxide changes.

If these preconditions are not fulfilled, a waiting time with constant pumping in air of 30 minutes has to be maintained. If thereafter the values (relative humidity, carbon-dioxide/air concentration) are still not fulfilled, the installation 10 delivers a fault signal to either the control 26 or other display and measuring is broken off.

If the air values fulfil the stated requirements, the bell 15 is lowered, preferably in regulated manner, to a lowered setting 27 of, for example, −4 cm into the process liquid 11 (bath or container). In that case, the change in the carbon dioxide concentration is determined in the projection of the bath under the bell 15. This carbon dioxide concentration is now recorded over a time period of several hours and monitored by algorithms. If within this time a specific value should be exceeded, the measurement is broken off, because then very high bacterial values are present.

After elapsing of a measuring time of approximately 10 hours the bell 15 is again lifted, preferably in regulated manner, into the raised setting at the position of +15 cm distance from the bath level (liquid surface 17).

Figure 2:
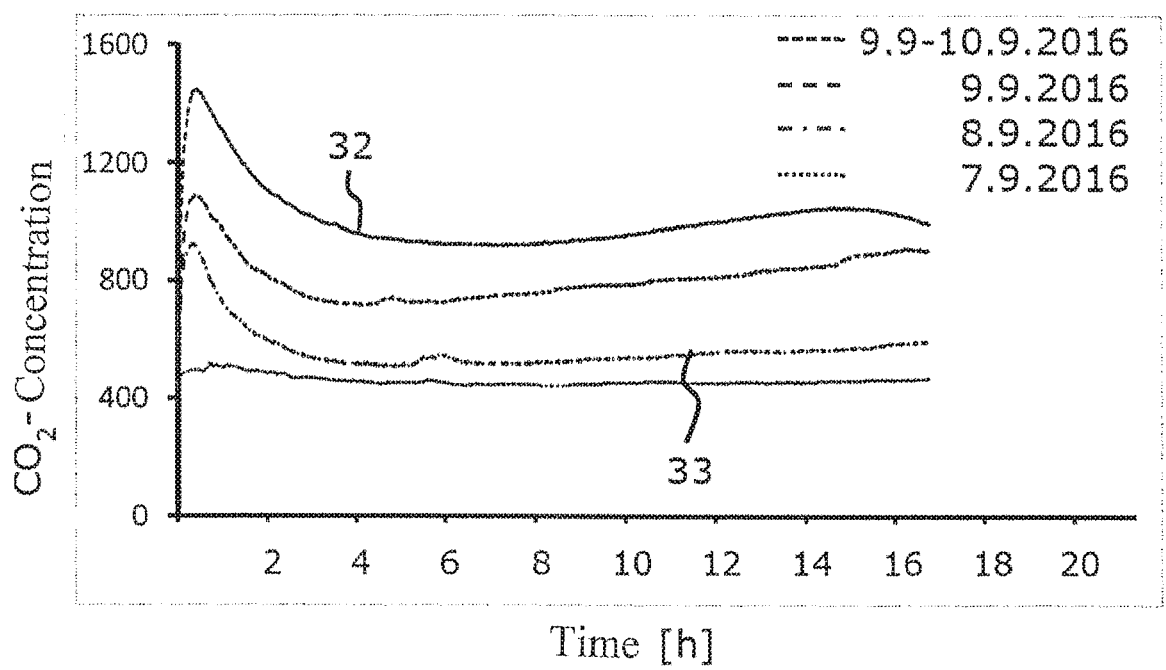
FIG. 2 shows four long-term measurements carried out each at an interval of approximately 24 hours.

FIG. 2 shows the carbon dioxide concentration plots from four long-term measurements which each were carried out at an interval of approximately 24 hours at a coating of a CDC plant. Each individual measurement has a duration of 16.5 hours. In the case of the last measurement (upper measurement curve 32), biocide was admetered after a time period of 7.5 hours. Accordingly, after 7.5 hours the carbon dioxide concentration dropped. The measuring device used for that purpose was equipped with three NDIR sensors (Non-Dispersive InfraRed sensors) for measuring the carbon dioxide concentration (signal averaging) in the coating.

The respective first peak has in each instance its origin in the carbon dioxide ($CO_2$) which was released into the coating and which was liberated by means of the agitator 24 (see "Short term measurement (rapid measurement)" and "Measurement cycle for rapid measurement").

The gradient between the 6th and 8th hour of the measuring time is available for evaluating the long-term measurement.

Algorithm 1:

Linear "fit" (straight line) through these two points (6 hours and 8 hours) and classification of different gradient regions, thus, for example, gradient 0: less bacteria even to the extent of no bacteria or no association with a bacterial count.

A difficulty with measurements of that kind at a plant is that a large amount of time has to be expended in order to catch the exact instant of plant bacterial contamination. In this case it occurs every 4-8 weeks, i.e. there is measurement, over as much time as possible, of curves such as shown in FIG. 2 at the lowermost measurement curve 33.

Algorithm 2:

Take the absolute value of the concentration after a specific number of hours of measuring time (xh) and then carry out classification.

Algorithm 3:

This applies only to very high concentrations in which the measured carbon dioxide concentration departs from the measurement range (0-2,000 ppm) of the gas sensors. Here the time until reaching 2,000 ppm is to be classified.

Measurement Cycle for Rapid Measurement:

The measurement cycle is identical until lowering of the bell 15. After lowering of the bell 15 into its lowered setting 27 the agitator 24 is started, for example at 400 rpm, so as to rapidly expel or be able to rapidly expel large quantities of carbon dioxide.

Algorithm 4:

Classification of the gradient and absolute value of the concentration at the instant of 10 minutes.

Algorithm 5:

Classification of the signal by the absolute value of the concentration at the crest of the curve ($f'(x) \cong 0$).

An exact classification with respect to bacterial count can take place, depending on use, only after a learning phase of the classifier and is obviously dependent on the fluid under investigation. However, quantitative statements can be made rapidly.

In order to monitor the degree of bacterial contamination of the process liquid 11 not only operation of the gas pump 14, but also generation of a signal by the at least one gas sensor 12 are carried out preferably continuously, thus free of interruption. The long-term measurements over the predetermined lengthy time are undertaken at predetermined, preferably periodic, time intervals. A short-term measurement is preferably also carried out at the start of each long-term measurement, for which purpose the agitator 24 is actuated for a predetermined short time. However, short-term measurements can be carried out alternatively or additionally at other time instants during the long-term measurement or also between successive long-term measurements. Both measurements can be carried out daily in alternation.

The classification and visualization take place by way of a single motherboard computer, which in the case of connection with the Internet uploads data into the Cloud so that the data can be retrieved wherever Internet access is present. Notification to a mobile telephone or to other IOT applications (IOT=Internet of Things) can be realized.

REFERENCE NUMERAL LIST

10 measuring apparatus/measuring system/plant
11 process liquid
12 sensor array/gas sensor array/gas sensor
13 evaluating device/evaluating unit
14 gas pump/diaphragm pump
15 gas collecting hollow body/gas collecting bell/bell
16 immersion cavity
17 liquid surface/liquid level
18 gas collection cavity
19 gas feed line
20 sensor device
21 gas return line
22 raising and lowering device
23 lowered position
24 agitator
25 interface
26 control/plant control
27 neck 28 funnel
29 funnel wall
30 edge
31 hose
32 upper measurement curve
33 lowermost measurement curve

What is claimed is:

1. A measuring apparatus (10) for determining the degree of bacterial contamination of a process liquid (11), comprising
    at least one gas sensor (12) for measuring a gas concentration of a gas producible or produced by aerobic bacteria possibly or actually present in the process liquid (11); and
    an evaluating device (13), which is connected therewith, configured to evaluate a sensor signal which is generated by the at least one gas sensor (12) and which is correlated with the degree of bacterial contamination, the evaluating device comprising a PC, a microcontroller, or a data logger;
    wherein a geometric gas collecting hollow body (15) is provided, which hollow body has an immersion cavity (16) and is partly immersible or immersed in the process liquid (11) in such a way that a gas collection cavity (18) for collecting a gas escaping from the process liquid (11) into the environment is formed in the gas collecting hollow body (15) above a liquid surface (17), which is present in the immersion cavity (16), of the process liquid (11);
    wherein a gas feed line (19) is provided, the gas feed line having a first feed line end communicating with the gas collection cavity (18) of the gas collecting hollow body (15) and a second feed line end communicating with a device cavity of a sensor device (20), which includes the at least one gas sensor (12) for measuring the concentration of the gas escaping from the process liquid (11) and which is in gas connection with the at least one gas sensor (12);
    wherein a gas return line (21) is provided, the gas return line (21) having a first return line end communicating with the device cavity of the sensor device (20) and a second return line end opening directly into the gas collection cavity (18) of the gas collecting hollow body (15); and
    wherein a gas pump (14) for pumping the gas from the gas collection cavity (18) of the gas collecting hollow body (15) by way of the at least one gas sensor (12) back to the gas collection cavity (18) of the gas collecting hollow body (15) is provided.

2. The measuring apparatus according to claim 1, wherein the gas collecting hollow body (15) is formed to be bell-shaped or funnel-shaped or as a bell or funnel.

3. The measuring apparatus according to claim 1, wherein an agitator (24) comprising a stirring element configured to homogenize the process liquid and/or an agitator (24) comprising a stirring element configured to expel the gas produced by the aerobic bacteria and released into the process liquid and/or configured to expel gas produced by the aerobic bacteria and adsorbed at solid particles contained in the process liquid (11) is or are provided.

4. The measuring apparatus according to claim 1, wherein a controllable raising and lowering device (22) for raising and lowering the gas collecting hollow body (15) and optionally the agitator (24) is provided, by means of which the gas collecting hollow body (15) and optionally the agitator (24) are movable from a raised setting outside the process liquid (11) to a lowered setting (23), in which the gas collecting hollow body (15) is partly and optionally the agitator (24) at least partly immersed in the process liquid (11) and in which the gas concentration of a gas produced by the bacteria is measurable by way of the at least one gas sensor (12), and by means of which the gas collecting hollow body (15) and optionally the agitator (24) are movable from the lowered setting (23) to the raised setting.

5. The measuring apparatus according to claim 4, wherein the controllable raising and lowering device (22) comprises a distance sensor for measuring the spacing of the gas collecting hollow body (15) from the liquid surface (17) of the process liquid (11).

6. The measuring apparatus according to claim 5, wherein the distance sensor is an ultrasonic sensor.

7. The measuring apparatus according to claim 1, wherein the evaluating device (13) is provided with an interface (25) for connection with a control (26) by means of which a biocide can be admetered to the process liquid (11) in dependence on the gas concentration, which is measured by way of the at least one gas sensor, of the gas produced over time by the bacteria or wherein the evaluating device (13) is connected directly or via the interface (25) with a control (26) by means of which a biocide can be admetered to the process liquid (11) in dependence on the gas concentration, which is measured by way of the at least one gas sensor (12), of the gas produced over time by the bacteria.

8. A method of determining the degree of bacterial contamination of process liquid,
    wherein a gas concentration of a gas producible or produced by bacteria possibly or actually present in a process liquid (11) is measured by way of at least one gas sensor (12) which produces a sensor signal correlated with the degree of bacterial contamination;
    wherein the sensor signal is evaluated by means of an evaluating device (13) connected with the at least one gas sensor (12), the evaluating device comprising a PC, a microcontroller, or a data logger;
    wherein a geometric gas collecting hollow body (15) having an immersion cavity (16) is partly immersed in the process liquid (11) in such a way that a gas collection cavity (18) for collecting a gas escaping from the process liquid (11) into the environment is formed in the gas collecting hollow body (15) above a liquid surface (17), which is present in the immersion cavity (16), of the process liquid (11);
    wherein the gas escaping from the process liquid (11) into the environment is collected in the gas collection cavity (18) and from there fed by means of a gas pump (14) via a gas feed line (19) to the at least one gas sensor (12), conducted via the at least one gas sensor (12) and pumped by way of a gas return line (21) opening directly into the gas collection cavity of the gas collecting hollow body back again to the gas collection cavity (18) of the gas collecting hollow body (15).

9. The method according to claim 8, wherein the gas collecting hollow body (15) is funnel-shaped or bell-shaped or is formed as a bell or funnel.

10. The method according to claim 8, wherein gas produced by aerobic bacteria and released into the process liquid (11) and/or gas produced by aerobic bacteria and adsorbed at solid particles contained in the process liquid (11) is or are expelled by means of an agitator (24) comprising a stirring element; and
    wherein a gas concentration of expelled gas is measured by way of the at least one gas sensor (12).

11. The method according to claim 8, wherein the gas collecting hollow body (15) and optionally an agitator (24)

are transferable by means of a controllable raising and lower device (22) from a lowered setting (23), in which the gas collecting hollow body (15) is partly and optionally the agitator (24) at least partly immersed in the process liquid (11) and in which the gas concentration of the gas produced by the bacteria is measured by way of the at least one gas sensor (12), to a raised setting, in which the gas collecting hollow body (15) and optionally the agitator (24) are disposed outside the process liquid (11), and conversely.

12. The method according to claim 11, wherein the gas collecting hollow body (15) and optionally the agitator (24) before being disposed in the lowered setting (23) thereof are moved by means of the controllable raising and lowering device (22), starting from the raised setting in which they are disposed outside the process liquid (11), to the lowered setting (22) in which the gas collecting hollow body (15) is partly and optionally the agitator (24) at least partly immersed in the process liquid (11).

13. The method according to claim 8, wherein the evaluating device (13) is connected directly or by way of an interface (25) with a control (26), by means of which a biocide is admetered to the process liquid (11) in dependence on the gas concentration, which is measured by way of the at least one gas sensor (12), of a gas produced over time by the bacteria.

14. The method according to claim 8, wherein the degree of bacterial contamination is determined by means of a measuring apparatus (10) comprising
- at least one gas sensor (12) for measuring the gas concentration of a gas producible or produced by aerobic bacteria possibly or actually present in the process liquid (11); and
- an evaluating device (13), which is connected therewith, configured to evaluate a sensor signal which is generated by the at least one gas sensor (12) and which is correlated with the degree of bacterial contamination;
- wherein a geometric gas collecting hollow body (15) is provided, which hollow body has an immersion cavity (16) and is partly immersible or immersed in the process liquid (11) in such a way that a gas collection cavity (18) for collecting the gas escaping from the process liquid (11) into the environment is formed in the gas collecting hollow body (15) above a liquid surface (17), which is present in the immersion cavity (16), of the process liquid (11);
- wherein a gas feed line (19) is provided, the gas feed line comprising a first feed line end communicating with the gas collection cavity (18) of the gas collecting hollow body (15) and a second feed line end communicating with a device cavity of a sensor device (20), which includes the at least one gas sensor (12) for measuring the concentration of the gas escaping from the process liquid (11) and which is in gas connection with the at least one gas sensor (12);
- wherein a gas return line (21) is provided, the gas return line comprising a first return line end communicating with the device cavity of the sensor device (20) and a second return line end communicating with the gas collection cavity (18) of the gas collecting hollow body (15); and
- wherein a gas pump (14) for pumping the gas from the gas collection cavity (18) of the gas collecting hollow body (15) by way of the at least one gas sensor (12) back to the gas collection cavity (18) of the gas collecting hollow body (15) is provided.

* * * * *